(12) United States Patent
Murakami et al.

(10) Patent No.: US 9,023,147 B2
(45) Date of Patent: May 5, 2015

(54) METHOD FOR PRODUCING RUTILE TYPE TITANIUM OXIDE SOL

(71) Applicant: Nissan Chemical Industries, Ltd., Tokyo (JP)

(72) Inventors: Natsumi Murakami, Sodegaura (JP); Ai Miyamoto, Sodegaura (JP); Yoshinari Koyama, Sodegaura (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 14/359,393

(22) PCT Filed: Nov. 30, 2012

(86) PCT No.: PCT/JP2012/081176
§ 371 (c)(1),
(2) Date: May 20, 2014

(87) PCT Pub. No.: WO2013/081136
PCT Pub. Date: Jun. 6, 2013

(65) Prior Publication Data
US 2014/0328889 A1   Nov. 6, 2014

(30) Foreign Application Priority Data

Dec. 2, 2011  (JP) ................. 2011-264664

(51) Int. Cl.
| | | |
|---|---|---|
| *C01G 23/053* | (2006.01) | |
| *B82Y 30/00* | (2011.01) | |
| *A01N 25/08* | (2006.01) | |
| *B01J 31/38* | (2006.01) | |
| *C09D 5/16* | (2006.01) | |
| *C09D 7/12* | (2006.01) | |

(52) U.S. Cl.
CPC ......... *C01G 23/053* (2013.01); *Y10T 428/2982* (2015.01); *C01P 2002/30* (2013.01); *C01P 2006/22* (2013.01); *C01P 2004/64* (2013.01); *B82Y 30/00* (2013.01); *A01N 25/08* (2013.01); *B01J 31/38* (2013.01); *C09D 5/1618* (2013.01); *C09D 7/1266* (2013.01); *G02B 1/111* (2013.01)

(58) Field of Classification Search
USPC .............................. 106/436, 459
See application file for complete search history.

(56) References Cited

U.S. PATENT DOCUMENTS

| | | | |
|---|---|---|---|
| 6,296,943 B1 | 10/2001 | Watanabe et al. | |
| 7,431,903 B2 * | 10/2008 | Koyanagi et al. | ............... 423/81 |
| 2006/0046504 A1 * | 3/2006 | Kayama et al. | ............... 438/758 |
| 2006/0110319 A1 * | 5/2006 | Seok et al. | .................... 423/610 |
| 2010/0148135 A1 | 6/2010 | Yokoyama | |

FOREIGN PATENT DOCUMENTS

| | | |
|---|---|---|
| JP | A-63-210027 | 8/1988 |
| JP | A-2-25532 | 1/1990 |
| JP | A-2-255532 | 10/1990 |
| JP | A-10-245224 | 9/1998 |
| JP | A-2005-132706 | 5/2005 |
| JP | 2006335619 A * | 12/2006 |
| JP | 2006342311 A * | 12/2006 |
| JP | A-2008-266043 | 11/2008 |
| JP | A-2009-227519 | 10/2009 |
| JP | A-2010-58031 | 3/2010 |
| JP | A-2010-138020 | 6/2010 |
| WO | WO 2007052580 A1 * | 5/2007 |

OTHER PUBLICATIONS

Feb. 5, 2013 Written Opinion of the International Searching Authority issued in International Application No. PCT/JP2012/081176.
Feb. 5, 2013 International Search Report issued in International Application No. PCT/JP2012/081176.

* cited by examiner

*Primary Examiner* — Anthony J Green
(74) *Attorney, Agent, or Firm* — Oliff PLC

(57) ABSTRACT

There is provided provide a method for efficiently producing a rutile type titanium sol having a particle diameter based on dynamic light scattering method of 5 nm to 100 nm that is excellent in dispersibility. The method for producing a rutile type titanium oxide sol comprising: process (a): mixing metastannic acid, a titanium alkoxide, a quaternary ammonium hydroxide, oxalic acid, and water so as to contain 0.02 moles to 0.8 moles of tin atoms, 0.1 moles to 3.5 moles of the quaternary ammonium hydroxide, and 0.1 moles to 8.0 moles of the oxalic acid with respect to 1 mole of titanium atoms of the titanium alkoxide to prepare a titanium-containing aqueous solution with a concentration in terms of $TiO_2$ of 0.1% by mass to 15% by mass; and process (b): subjecting the titanium-containing aqueous solution obtained in process (a) to a hydrothermal treatment at a temperature from 100° C. to 170° C.

4 Claims, No Drawings

METHOD FOR PRODUCING RUTILE TYPE TITANIUM OXIDE SOL

TECHNICAL FIELD

The present invention relates to a method for producing a rutile type titanium oxide sol.

BACKGROUND ART

There are three types of crystal structures of titanium oxide, that is, the tetragonal, high-temperature rutile type, the tetragonal, low-temperature anatase type, and the orthorhombic brookite type. Among these, the rutile type titanium oxide has been used as refractive index regulators because of its high refractive index.

In order to be used as optical materials, the rutile type titanium oxide is required to have transparency when being formed as a coating film as well as a high refractive index. However, the rutile type titanium oxide is generally produced by a solid phase process in which amorphous titanium oxide or anatase type titanium oxide is baked at a high temperature, and the particle diameter disadvantageously increases, thereby transparency is impaired.

Compared with the solid phase process that requires high-temperature baking, a wet process is a method by which fine particles can be easily obtained, because they can be synthesized at a low temperature.

Examples of the method for producing the rutile type titanium oxide by the wet process may include a method in which a titanium salt and a tin compound having the rutile type structure are reacted in a coexistent manner.

As the method that uses the titanium salt and the tin compound, a method is disclosed in which a strong acid salt of titanium and metallic tin are reacted in the presence of hydrogen peroxide to produce an aggregate of a composite colloid of titanium oxide and tin oxide at a temperature from 50° C. to 100° C. (refer to Patent Document 1).

A method is disclosed for producing rutile type titanium oxide fine particles, in which a titanium compound solution coexisting with a tin compound at a Sn/Ti molar ratio of 0.001 to 2 is reacted within a pH range of 1 to 3 at a temperature from room temperature to 100° C. (refer to Patent Document 2).

Another method for obtaining a rutile type titanium oxide sol is a method in which a gel containing titanium atoms is dissolved in hydrogen peroxide and is then reacted with a tin compound or the like; specific examples of the method include a method in which hydrogen peroxide dissolving a hydrated titanium oxide gel and cation-exchanged potassium stannate are mixed and subjected to a heat treatment (refer to Patent Document 3) and a method in which a titanium compound, a tin compound, and ammonia are reacted to form a gel, which is then dissolved in hydrogen peroxide to be subjected to a hydrothermal treatment (refer to Patent Document 4).

PRIOR ART DOCUMENTS

Patent Documents

Patent Document 1: Japanese Patent Application Publication No. H10-245224 (JP H10-245224 A)
Patent Document 2: Japanese Patent Application Publication No. 2005-132706 (JP 2005-132706 A)
Patent Document 3: Japanese Patent Application Publication No. H02-25532 (JP H02-25532 A)
Patent Document 4: Japanese Patent Application Publication No. 2009-227519 (JP 2009-227519 A)

SUMMARY OF THE INVENTION

Problems to be Solved by the Invention

The method disclosed in Patent Document 1 produces aggregate slurry of composite colloidal particles of titanium oxide and tin oxide with a primary particle diameter of 2 nm to 20 nm, and a contained electrolyte is required to be removed so that a favorably dispersed gel is obtained. The method disclosed in Patent Document 2 produces precipitates and requires a solid-liquid separator. The method disclosed in Patent Document 3 makes it difficult to prepare a stable gel or sol of hydrated titanium oxide having a high specific surface area, which results in fluctuation of the crystallinity of the obtained titanium oxide. In addition, impurities such as alkali remain in the gel or sol of hydrated titanium oxide, and rutile type titanium oxide that does not contain substantially any alkali cannot be obtained. The method disclosed in Patent Document 4 requires washing a mixed gel of a titanium hydroxide and a tin hydroxide. The method is not industrially preferable, because it is difficult to remove impurity ions, the washing takes a long time, and a solid-liquid separator is required.

The present invention provides a method for efficiently producing a rutile type titanium sol having a particle diameter based on dynamic light scattering method of 5 nm to 100 nm that does not contain substantially any impurities such as alkali metal ions such as sodium and potassium and chloride ions, does not require a solid-liquid separating process, and is excellent in dispersibility.

Means for Solving the Problems

The inventors of the present invention have earnestly studied to solve the above problems and have found out that a favorably dispersed rutile type titanium oxide sol can be produced without producing precipitates and aggregates by subjecting a titanium-containing aqueous solution containing a tin salt, oxalic acid, and a quaternary ammonium hydroxide to a hydrothermal treatment. The present invention relates to, as a first aspect, a method for producing a rutile type titanium oxide sol having a particle diameter based on dynamic light scattering method of 5 nm to 100 nm, comprising:

process (a): mixing metastannic acid, a titanium alkoxide, a quaternary ammonium hydroxide, oxalic acid, and water so as to contain 0.02 moles to 0.8 moles of tin atoms, 0.1 moles to 3.5 moles of the quaternary ammonium hydroxide, and 0.1 moles to 8.0 moles of the oxalic acid with respect to 1 mole of titanium atoms of the titanium alkoxide to prepare a titanium-containing aqueous solution with a concentration in terms of $TiO_2$ of 0.1% by mass to 15% by mass; and process (b): subjecting the titanium-containing aqueous solution obtained in process (a) to a hydrothermal treatment at a temperature from 100° C. to 170° C., as a second aspect, the method for producing a rutile type titanium oxide sol according to the first aspect, in which the titanium alkoxide is a titanium tetraalkoxide of General Formula (I):

$$Ti(OR^1)_4 \quad \text{(I)}$$

(where $R^1$ are each a $C_{1-3}$ alkyl group and are the same or different), as a third aspect, the method for producing a rutile type titanium oxide sol according to the first aspect, in which the quaternary ammonium hydroxide is a quaternary ammonium hydroxide of General Formula (II):

$$[NR^2R^3R^4R^5]OH \qquad (II)$$

(where $R^2$, $R^3$, $R^4$, and $R^5$ are each independently a $C_{1-8}$ alkyl group, a $C_{1-8}$ hydroxyalkyl group, a $C_{7-15}$ aryloxyalkyl group, or a benzyl group), and as a fourth aspect, the method for producing a rutile type titanium oxide sol according to the first aspect, in which the quaternary ammonium hydroxide is tetramethylammonium hydroxide or tetraethylammonium hydroxide.

Effects of the Invention

The rutile type titanium oxide sol obtained by the present invention does not contain substantially any impurities such as alkali metal ions such as sodium and potassium and chloride ions, and has high transparency.

The rutile type titanium oxide sol obtained by the present invention can be formed into a coating composition by being mixed with various binders and can be formed into a coating film having high transparency that does not impair the transparency of a substrate and a high refractive index by being applied onto the substrate.

MODES FOR CARRYING OUT THE INVENTION

In the present invention, first in process (a), metastannic acid, a titanium alkoxide, a quaternary ammonium hydroxide, oxalic acid, and water are mixed and a titanium-containing aqueous solution is prepared.

The respective ratios of metastannic acid, the titanium alkoxide, the quaternary ammonium hydroxide, and oxalic acid to be mixed are adjusted so that the resultant aqueous solution contains 0.02 moles to 0.8 moles of tin atoms, 0.1 moles to 3.5 moles of the quaternary ammonium hydroxide, and 0.1 moles to 8.0 moles of the oxalic acid with respect to 1 mole of titanium atoms of the titanium alkoxide.

Tin atoms are adjusted to be 0.02 moles to 0.8 moles with respect to 1 mole of the titanium atoms of the titanium alkoxide. When the molar ratio is less than 0.02, the crystallinity of the rutile type titanium oxide is insufficient, and anatase type titanium oxide may be produced. When the molar ratio exceeds 0.8, the content of tin oxide in the obtained rutile type titanium oxide increases and the refractive index of the obtained titanium oxide decreases, which is not preferable.

The quaternary ammonium hydroxide is adjusted to be 0.1 moles to 3.5 moles with respect to 1 mole of the titanium atoms of the titanium alkoxide. When the molar ratio is less than 0.1 moles, a mixture of the rutile type and the anatase type titanium oxide whose particle diameter based on dynamic light scattering method exceeds 100 nm is produced after a hydrothermal treatment in process (b), and the target single-phase rutile type titanium oxide sol cannot be obtained. When the quaternary ammonium hydroxide exceeds 3.5 moles with respect to 1 mole of the titanium atoms of the titanium alkoxide, after the hydrothermal process in process (b), no colloidal particles are produced to be a solution, and the rutile type titanium hydroxide sol cannot be obtained.

Oxalic acid is adjusted to be 0.1 moles to 8.0 moles with respect to 1 mole of the titanium atoms of the titanium alkoxide. When the molar ratio is less than 0.1 moles, a mixture of the rutile type and the anatase type titanium oxide whose particle diameter based on dynamic light scattering method exceeds 100 nm is produced after the hydrothermal treatment in process (b), and the target rutile type titanium oxide sol cannot be obtained. When oxalic acid exceeds 8.0 moles with respect to 1 mole of the titanium atoms of the titanium alkoxide, the rutile type titanium oxide sol whose particle diameter based on dynamic light scattering method of 100 nm or less can be obtained, but which only consumes excessive oxalic acid and thus is uneconomical.

In process (a), the titanium-containing aqueous solution is prepared so as to be 0.1% by mass to 15% by mass and preferably 1% by mass to 10% by mass in terms of $TiO_2$ by appropriately adjusting the amount of water.

It is preferable that the mixing of metastannic acid, the titanium alkoxide, oxalic acid, the quaternary ammonium hydroxide, and water be performed with stirring. It is more preferable that metastannic acid be added to an aqueous solution of the quaternary ammonium hydroxide, the titanium alkoxide be then added thereto, and oxalic acid be lastly added thereto. The titanium-containing aqueous solution may be heated at a temperature from 60° C. to 100° C. before being subjected to the hydrothermal treatment in process (b).

The pH of the titanium-containing aqueous solution prepared in process (a) is 1.0 to 14.0.

The titanium alkoxide used in the present invention is a titanium tetraalkoxide having $C_{1-3}$ alkoxy groups. This titanium tetraalkoxide can be represented by General Formula (I):

$$Ti(OR^1)_4 \qquad (I)$$

(where $R^1$ are each a $C_{1-3}$ alkyl group and are the same or different).

In the titanium tetraalkoxide, the four alkoxy groups may be the same or different; in view of the ease of availability, the same ones are preferably used. Specific examples of the titanium tetraalkoxide include titanium tetramethoxide, titanium tetraethoxide, titanium tetra-n-propoxide, and titanium tetra-isopropoxide. One of them may be used singly, or two or more of them may be used in combination.

The quaternary ammonium hydroxide used in the present invention is represented by General Formula (II):

$$[NR^2R^3R^4R^5]OH \qquad (II)$$

(where $R^2$, $R^3$, $R^4$, and $R^5$ are each independently a $C_{1-8}$ alkyl group, a $C_{1-8}$ hydroxyalkyl group, a $C_{7-15}$ aryloxyalkyl group, or a benzyl group).

Specific examples of the quaternary ammonium hydroxide include tetramethylammonium hydroxide, tetraethylammonium hydroxide, tetrapropylammonium hydroxide, tetrabutylammonium hydroxide, octyltrimethylammonium hydroxide, tributylmethylammonium hydroxide, trioctylmethylammonium hydroxide, benzyltrimethylammonium hydroxide, benzyltriethylammonium hydroxide, benzyltripropylammonium hydroxide, benzyltributylammonium hydroxide, monomethyltriethanolammonium hydroxide, and dimethyldiethanolammonium hydroxide. Among them, tetramethylammonium hydroxide or tetraethylammonium hydroxide are preferably used.

In process (a), the added titanium alkoxide is decomposed to produce alcohol. The alcohol as a byproduct may be or may not be removed. When the alcohol is removed, the titanium-containing aqueous solution may be heated at a temperature above the boiling point of the alcohol or the alcohol may be distilled off under reduced pressure using an evaporator or the like.

The titanium-containing aqueous solution obtained in process (a) is charged into a pressure-resistant vessel and is subjected to the hydrothermal treatment to produce the rutile type titanium oxide sol having a particle diameter based on dynamic light scattering method of 5 nm to 100 nm. The hydrothermal treatment temperature is 100° C. to 170° C. and is preferably 120° C. to 160° C. The hydrothermal treatment time is 0.5 hours to 10 hours and is preferably 1 hour to 6 hours. When the hydrothermal treatment temperature is less than 100° C., the crystallization of titanium oxide fine particles is insufficient, whereas when the hydrothermal treatment temperature exceeds 170° C., the produced titanium oxide fine particles aggregate, which unfortunately requires a dispersing treatment with a homogenizer or the like to obtain a sol.

In the International Centre for Diffraction Data (ICDD) card, the value of the interplanar spacing d (Å) of the <110> planes of titanium oxide is 3.35, whereas the value d of the <110> planes of the rutile type titanium oxide is 3.25. The rutile type titanium oxide obtained by the present invention is found to be a single-phase rutile type crystal, based on a diffraction pattern from powder X-ray diffraction analysis and the value d of the <110> planes satisfying 3.25<d<3.35.

The rutile type titanium oxide sol obtained by process (a) and process (b) is observed with a transmission electron microscope as ellipsoidal-spherical colloidal particles whose primary particle diameter is 5 nm to 50 nm in a projection image. The obtained rutile type titanium oxide sol has a particle diameter of 5 nm to 100 nm, measured by a dynamic light scattering particle diameter measuring apparatus.

The rutile type titanium oxide sol obtained by the present invention has high transparency, and no sediment is observed even after the sol is left at rest for a week at room temperature.

The rutile type titanium oxide sol obtained by the present invention has a pH within the range of 1.0 to 14.0.

The rutile type titanium oxide sol obtained by the present invention can be washed and/or concentrated using the ultrafiltration technique. Pure water can be used for washing. The sol can be concentrated by ultrafiltration up to around 40% by mass in terms of $TiO_2$.

The rutile type titanium oxide sol obtained by the present invention can be further stabilized as a sol by adding an acid, a base, or a surfactant singly or in combination as needed.

Examples of acids used include inorganic acids such as hydrochloric acid and sulfuric acid and organic acids such as oxalic acid, lactic acid, tartaric acid, malic acid, citric acid, glycolic acid, hydroacrylic acid, α-hydroxybutyric acid, glyceric acid, and tartronic acid.

Examples of bases used include ammonia, alkali metal hydroxides, alkylamines such as ethylamine, diethylamine, n-propylamine, isopropylamine, diisopropylamine, dipropylamine, n-butylamine, isobutylamine, diisobutylamine, triethylamine, and benzylamine; alkanolamines such as monoethanolamine and triethanolamine; quaternary ammonium hydroxides such as guanidine hydroxide, tetramethylammonium hydroxide, and tetraethylammonium hydroxide; and carbonates such as ammonium carbonate and guanidine carbonate.

Examples of the surfactants used include anionic, cationic, and nonionic surfactants. Specific examples of the surfactants include Disperbyk-180 (manufactured by BYK-Chemie Japan K.K.), Disperbyk-191 (manufactured by BYK-Chemie Japan K.K.), Disperbyk-2091 (manufactured by BYK-Chemie Japan K.K.), BYK-301/302 (manufactured by BYK-Chemie Japan K.K.), BYK-331 (manufactured by BYK-Chemie Japan K.K.), and BYK-347 (manufactured by BYK-Chemie Japan K.K.).

The rutile type titanium oxide sol obtained by the present invention can be mixed with various binders to form a coating composition. Examples of the binders used include organic silicone compounds such as tetramethoxysilane, tetraethoxysilane, tetra-n-propoxysilane, tetra-n-butoxysilane, methyltrimethoxysilane, γ-glycidoxypropyltrimethoxysilane, γ-glycidoxypropyltriethoxysilane, ethyltrimethoxysilane, ethyltriethoxysilane, vinyltrimethoxysilane, vinyltriethoxysilane, phenyltriethoxysilane, γ-chloropropyltrimethoxysilane, γ-chloropropyltriethoxysilane, and γ-aminopropyltriethoxysilane.

The coating composition can be applied onto a substrate to obtain a member having a high refractive index coating. Examples of the substrate include plastic, rubber, glass, metal, ceramics, and paper.

The refractive index of the coating varies in accordance with the mixing ratio of the rutile type titanium oxide sol and a binder and the type of the binder, and is approximately within the range of 1.55 to 2.2.

An anti-reflective coating may be further formed on the coating having a high refractive index obtained by applying the coating composition containing the rutile type titanium oxide sol obtained by the present invention and the binder, thereby providing an anti-reflective function.

EXAMPLES

The following describes the present invention specifically with reference to examples and comparative examples. The present invention is not limited to these examples.

Example 1

79.0 g of pure water was put into a 200 ml beaker, in which mixed with stirring were 0.89 g of metastannic acid (manufactured by Showa Kako Corporation, contained in an amount of 0.75 g in terms of $SnO_2$), 4.6 g of 25% by mass tetramethylammonium hydroxide aqueous solution, 1.2 g of oxalic acid dihydrate (manufactured by Ube Industries, Ltd., contained in an amount of 0.9 g in terms of oxalic acid), and 14.3 g of titanium tetraisopropoxide (contained in an amount of 4 g in terms of $TiO_2$). The resultant titanium-containing aqueous solution had a tin atom/titanium atom molar ratio of 0.1, a tetramethylammonium hydroxide/titanium atom molar ratio of 0.25, and an oxalic acid/titanium atom molar ratio of 0.19. 100 g of the titanium-containing aqueous solution was heated at 80° C. for 2 hours. The heated titanium-containing aqueous solution had a pH of 4.2, an electric conductivity of 7.7 mS/cm, and a $TiO_2$ concentration of 4.0% by mass. 60 g of the heated titanium-containing aqueous solution was charged into a 100 ml Teflon (registered trademark) autoclave, was subjected to a hydrothermal treatment at 140° C. for 5 hours, and was cooled to room temperature after the hydrothermal treatment. The solution after the hydrothermal treatment was a pale milk white titanium oxide hydrosol. The resultant sol had a pH of 3.8, an electric conductivity of 8.1 mS/cm, a $TiO_2$ concentration of 4.0% by mass, 1.1% by mass of tetramethylammonium hydroxide, 0.9% by mass of oxalic acid, and a particle diameter based on dynamic light scattering method of 17 nm. Transmission electron microscope observation of the sol showed ellipsoidal particles with a minor axis of 5 nm and a major axis of 25 nm. X-ray diffraction analysis on powder obtained by drying the resultant sol at 110° C. revealed that the interplanar spacing d of the <110> planes was 3.26 Å and that the powder was a single phase of a rutile type crystal.

Example 2

80.6 g of pure water was put into a 200 ml beaker, in which mixed with stirring were 0.22 g of metastannic acid (contained in an amount of 0.19 g in terms of $SnO_2$), 4.6 g of 25% by mass tetramethylammonium hydroxide aqueous solution, 11.0 g of oxalic acid dihydrate (contained in an amount of 7.9 g in terms of oxalic acid), and 3.6 g of titanium tetraisopropoxide (contained in an amount of 1.0 g in terms of $TiO_2$). The resultant titanium-containing aqueous solution had a tin atom/titanium atom molar ratio of 0.1, a tetramethylammonium hydroxide/titanium atom molar ratio of 1.0, and an oxalic acid/titanium atom molar ratio of 7.0. 100 g of the titanium-containing aqueous solution was heated at 80° C. for 2 hours. The heated titanium-containing aqueous solution had a pH of 1.4, an electric conductivity of 43.2 mS/cm, and a $TiO_2$ concentration of 1.0% by mass. 60 g of the heated titanium-containing aqueous solution was charged into a 100 ml Teflon (registered trademark) autoclave, was subjected to a hydrothermal treatment at 140° C. for 5 hours, and was then cooled to room temperature after the hydrothermal treatment. The solution after the hydrothermal treatment was a pale milk white titanium oxide hydrosol. The resultant sol had a pH of 1.4, an electric conductivity of 43.2 mS/cm, a $TiO_2$ concentration of 1.0% by mass, 1.1% by mass of tetramethylammonium hydroxide, 7.9% by mass of oxalic acid, and a particle diameter based on dynamic light scattering method of 43 nm. Transmission electron microscope observation of the sol showed ellipsoidal particles with a minor axis of 5 nm and a major axis of 15 nm. X-ray diffraction analysis on powder obtained by drying the resultant sol at 110° C. revealed that the interplanar spacing d of the <110> planes was 3.26 Å and that the powder was a single phase of a rutile type crystal.

Example 3

62.0 g of pure water was put into a 200 ml beaker, in which mixed with stirring were 0.44 g of metastannic acid (contained in an amount of 0.38 g in terms of $SnO_2$), 27.3 g of 25% by mass tetramethylammonium hydroxide aqueous solution, 3.2 g of oxalic acid dihydrate (contained in an amount of 2.3 g in terms of oxalic acid), and 7.1 g of titanium tetraisopropoxide (contained in an amount of 2.0 g in terms of $TiO_2$). The resultant titanium-containing aqueous solution had a tin atom/titanium atom molar ratio of 0.1, a tetramethylammonium hydroxide/titanium atom molar ratio of 3.0, and an oxalic acid/titanium atom molar ratio of 1.0. 100 g of the titanium-containing aqueous solution was heated at 80° C. for 2 hours. The heated titanium-containing aqueous solution had a pH of 13.5, an electric conductivity of 32.9 mS/cm, and a $TiO_2$ concentration of 2.0% by mass. 60 g of the heated titanium-containing aqueous solution was charged into a 100 ml Teflon (registered trademark) autoclave, was subjected to a hydrothermal treatment at 140° C. for 5 hours, and was then cooled to room temperature after the hydrothermal treatment. The solution after the hydrothermal treatment was a pale milk white titanium oxide hydrosol. The resultant sol had a pH of 14.0, an electric conductivity of 38.0 mS/cm, a $TiO_2$ concentration of 2.0% by mass, 6.8% by mass of tetramethylammonium hydroxide, 2.3% by mass of oxalic acid, and a particle diameter based on dynamic light scattering method of 28 nm. Transmission electron microscope observation of the sol showed ellipsoidal particles of 25 nm. X-ray diffraction analysis on powder obtained by drying the resultant sol at 110° C. revealed that the interplanar spacing d of the <110> planes was 3.27 Å and that the powder was a single phase of a rutile type crystal.

Example 4

62.0 g of pure water was put into a 200 ml beaker, in which mixed with stirring were 0.89 g of metastannic acid (contained in an amount of 0.75 g in terms of $SnO_2$), 18.2 g of 25% by mass tetramethylammonium hydroxide aqueous solution, 4.7 g of oxalic acid dihydrate (contained in an amount of 3.4 g in terms of oxalic acid), and 14.2 g of titanium tetraisopropoxide (contained in an amount of 4.0 g in terms of $TiO_2$). The resultant titanium-containing aqueous solution had a tin atom/titanium atom molar ratio of 0.1, a tetramethylammonium hydroxide/titanium atom molar ratio of 1.0, and an oxalic acid/titanium atom molar ratio of 0.75. 100 g of the titanium-containing aqueous solution was heated at 80° C. for 2 hours. The heated titanium-containing aqueous solution had a pH of 5.5, an electric conductivity of 13.6 mS/cm, and a $TiO_2$ concentration of 4.0% by mass. 60 g of the heated titanium-containing aqueous solution was charged into a 100 ml Teflon (registered trademark) autoclave, was subjected to a hydrothermal treatment at 140° C. for 5 hours, and was then cooled to room temperature after the hydrothermal treatment. The solution after the hydrothermal treatment was a pale milk white titanium oxide hydrosol. The resultant sol had a pH of 3.9, an electric conductivity of 18.7 mS/cm, a $TiO_2$ concentration of 4.0% by mass, 4.6% by mass of tetramethylammonium hydroxide, 3.4% by mass of oxalic acid, and a particle diameter based on dynamic light scattering method of 14 nm. Transmission electron microscope observation of the sol showed ellipsoidal particles with a minor axis of 5 nm and a major axis of 15 nm. X-ray diffraction analysis on powder obtained by drying the resultant sol at 110° C. revealed that the interplanar spacing d of the <110> planes was 3.26 Å and that the powder was a single phase of a rutile type crystal.

Example 5

71.5 g of pure water was put into a 200 ml beaker, in which mixed with stirring were 0.22 g of metastannic acid (contained in an amount of 0.19 g in terms of $SnO_2$), 13.7 g of 25% by mass tetramethylammonium hydroxide aqueous solution, 11.0 g of oxalic acid dihydrate (contained in an amount of 7.9 g in terms of oxalic acid), and 3.6 g of titanium tetraisopropoxide (contained in an amount of 1.0 g in terms of $TiO_2$). The resultant titanium-containing aqueous solution had a tin atom/titanium atom molar ratio of 0.1, a tetramethylammonium hydroxide/titanium atom molar ratio of 3.0, and an oxalic acid/titanium atom molar ratio of 7.0. 100 g of the titanium-containing aqueous solution was heated at 80° C. for 2 hours. The heated titanium-containing aqueous solution had a pH of 1.3, an electric conductivity of 53.9 mS/cm, and a $TiO_2$ concentration of 1.0% by mass. 60 g of the heated titanium-containing aqueous solution was charged into a 100 ml Teflon (registered trademark) autoclave, was subjected to a hydrothermal treatment at 140° C. for 5 hours, and was then cooled to room temperature after the hydrothermal treatment. The solution after the hydrothermal treatment was a pale milk white titanium oxide hydrosol. The resultant sol had a pH of 1.5, an electric conductivity of 35.0 mS/cm, a $TiO_2$ concentration of 1.0% by mass, 3.4% by mass of tetramethylammonium hydroxide, 7.9% by mass of oxalic acid, and a particle diameter based on dynamic light scattering method of 19 nm. Transmission electron microscope observation of the sol showed ellipsoidal particles with a minor axis of 10 nm and a major axis of 25 nm. X-ray diffraction analysis on powder obtained by drying the resultant sol at 110° C. revealed that the interplanar spacing d of the <110> planes was 3.26 Å and that the powder was a single phase of a rutile type crystal.

Example 6

62.5 g of pure water was put into a 200 ml beaker, in which mixed with stirring were 0.44 g of metastannic acid (contained in an amount of 0.38 g in terms of SnO$_2$), 18.2 g of 25% by mass tetramethylammonium hydroxide aqueous solution, 4.7 g of oxalic acid dihydrate (contained in an amount of 3.4 g in terms of oxalic acid), and 14.2 g of titanium tetraisopropoxide (contained in an amount of 4.0 g in terms of TiO$_2$). The resultant titanium-containing aqueous solution had a tin atom/titanium atom molar ratio of 0.05, a tetramethylammonium hydroxide/titanium atom molar ratio of 1.0, and an oxalic acid/titanium atom molar ratio of 0.75. 100 g of the titanium-containing aqueous solution was heated at 80° C. for 2 hours. The heated titanium-containing aqueous solution had a pH of 5.5, an electric conductivity of 17.7 mS/cm, and a TiO$_2$ concentration of 4.0% by mass. 60 g of the heated titanium-containing aqueous solution was charged into a 100 ml Teflon (registered trademark) autoclave, was subjected to a hydrothermal treatment at 140° C. for 5 hours, and was then cooled to room temperature after the hydrothermal treatment. The solution after the hydrothermal treatment was a pale milk white titanium oxide hydrosol. The resultant sol had a pH of 4.0, an electric conductivity of 23.8 mS/cm, a TiO$_2$ concentration of 4.0% by mass, 4.6% by mass of tetramethylammonium hydroxide, 3.4% by mass of oxalic acid, and a particle diameter based on dynamic light scattering method of 15 nm. Transmission electron microscope observation of the sol showed ellipsoidal particles with a minor axis of 5 nm and a major axis of 15 nm. X-ray diffraction analysis on powder obtained by drying the resultant sol at 110° C. revealed that the interplanar spacing d of the <110> planes was 3.29 Å and that the powder was a single phase of a rutile type crystal.

Example 7

56.7 g of pure water was put into a 200 ml beaker, in which mixed with stirring were 6.2 g of metastannic acid (contained in an amount of 5.3 g in terms of SnO$_2$), 18.2 g of 25% by mass tetramethylammonium hydroxide aqueous solution, 4.7 g of oxalic acid dihydrate (contained in an amount of 3.4 g in terms of oxalic acid), and 14.2 g of titanium tetraisopropoxide (contained in an amount of 4.0 g in terms of TiO$_2$). The resultant titanium-containing aqueous solution had a tin atom/titanium atom molar ratio of 0.7, a tetramethylammonium hydroxide/titanium atom molar ratio of 1.0, and an oxalic acid/titanium atom molar ratio of 0.75. 100 g of the titanium-containing aqueous solution was heated at 80° C. for 2 hours. The heated titanium-containing aqueous solution had a pH of 5.5, an electric conductivity of 19.1 mS/cm, and a TiO$_2$ concentration of 4.0% by mass. 60 g of the heated titanium-containing aqueous solution was charged into a 100 ml Teflon (registered trademark) autoclave, was subjected to a hydrothermal treatment at 140° C. for 5 hours, and was then cooled to room temperature after the hydrothermal treatment. The solution after the hydrothermal treatment was a pale milk white titanium oxide hydrosol. The resultant sol had a pH of 4.0, an electric conductivity of 23.2 mS/cm, a TiO$_2$ concentration of 4.0% by mass, 4.6% by mass of tetramethylammonium hydroxide, 3.4% by mass of oxalic acid, and a particle diameter based on dynamic light scattering method of 22 mu. Transmission electron microscope observation of the sol showed ellipsoidal particles of 10 nm. X-ray diffraction analysis on powder obtained by drying the resultant sol at 110° C. revealed that the interplanar spacing d of the <110> planes was 3.29 Å and that the powder was a single phase of a rutile type crystal.

Example 8

94.8 g of pure water was put into a 200 ml beaker, in which mixed with stirring were 0.22 g of metastannic acid (contained in an amount of 0.19 g in terms of SnO$_2$), 1.1 g of 25% by mass tetramethylammonium hydroxide aqueous solution, 0.30 g of oxalic acid dihydrate (contained in an amount of 0.21 g in terms of oxalic acid), and 3.6 g of titanium tetraisopropoxide (contained in an amount of 1.0 g in terms of TiO$_2$). The resultant titanium-containing aqueous solution had a tin atom/titanium atom molar ratio of 0.1, a tetramethylammonium hydroxide/titanium atom molar ratio of 0.25, and an oxalic acid/titanium atom molar ratio of 0.19. 100 g of the titanium-containing aqueous solution was heated at 80° C. for 2 hours. The heated titanium-containing aqueous solution had a pH of 5.0, an electric conductivity of 7.8 mS/cm, and a TiO$_2$ concentration of 1.0% by mass. 60 g of the heated titanium-containing aqueous solution was charged into a 100 ml Teflon (registered trademark) autoclave, was subjected to a hydrothermal treatment at 100° C. for 5 hours, and was then cooled to room temperature after the hydrothermal treatment. The solution after the hydrothermal treatment was a pale milk white titanium oxide hydrosol. The resultant sol had a pH of 5.4, an electric conductivity of 8.9 mS/cm, a TiO$_2$ concentration of 1.0% by mass, 0.28% by mass of tetramethylammonium hydroxide, 0.21% by mass of oxalic acid, and a particle diameter based on dynamic light scattering method of 27 nm. Transmission electron microscope observation of the sol showed ellipsoidal particles with a minor axis of 5 and a major axis of 15 nm. X-ray diffraction analysis on powder obtained by drying the resultant sol at 110° C. revealed that the interplanar spacing d of the <110> planes was 3.27 Å and that the powder was a single phase of a rutile type crystal.

Comparative Example 1

66.7 g of pure water was put into a 200 ml beaker, in which mixed with stirring were 0.89 g of metastannic acid (contained in an amount of 0.75 g in terms of SnO$_2$), 18.2 g of 25% by mass tetramethylammonium hydroxide aqueous solution, and 14.2 g of titanium tetraisopropoxide (contained in an amount of 4.0 g in terms of TiO$_2$). The resultant titanium-containing aqueous solution had a tin atom/titanium atom molar ratio of 0.1 and a tetramethylammonium hydroxide/titanium atom molar ratio of 1.0. 100 g of the titanium-containing aqueous solution was heated at 80° C. for 2 hours. The heated titanium-containing aqueous solution had a pH of 13.5, an electric conductivity of 27.1 mS/cm, and a TiO$_2$ concentration of 4.0% by mass. 60 g of the heated titanium-containing aqueous solution was charged into a 100 ml Teflon (registered trademark) autoclave, was subjected to a hydrothermal treatment at 140° C. for 5 hours, and was then cooled to room temperature after the hydrothermal treatment. The solution after the hydrothermal treatment was a pale white suspension. The resultant suspension had a pH of 13.7, an electric conductivity of 33.7 mS/cm, a TiO$_2$ concentration of 4.0% by mass, 4.6% by mass of tetramethylammonium hydroxide, and a particle diameter based on dynamic light scattering method of 115 nm. Transmission electron microscope observation of the suspension showed an aggregate of ellipsoidal particles of about 25 nm and fine particles of about 5 nm. X-ray diffraction analysis on powder obtained by drying the resultant sol at 110° C. revealed that the powder was a mixture of a rutile type crystal and an anatase type crystal.

Comparative Example 2

78.6 g of pure water was put into a 200 ml beaker, in which mixed with stirring were 0.89 g of metastannic acid (contained in an amount of 0.75 g in terms of SnO$_2$), 6.3 g of oxalic acid dihydrate (contained in an amount of 4.5 g in terms of oxalic acid), and 14.2 g of titanium tetraisopropoxide (contained in an amount of 4.0 g in terms of $TiO_2$). The resultant titanium-containing aqueous solution had a tin atom/titanium atom molar ratio of 0.1 and an oxalic acid/titanium atom molar ratio of 1.0. 100 g of the titanium-containing aqueous solution was heated at 80° C. for 2 hours. The heated titanium-containing aqueous solution had a pH of 1.1, an electric conductivity of 67.6 mS/cm, and a $TiO_2$ concentration of 4.0% by mass. 60 g of the heated titanium-containing aqueous solution was charged into a 100 nil Teflon (registered trademark) autoclave, was subjected to a hydrothermal treatment at 140° C. for 5 hours, and was then cooled to room temperature after the hydrothermal treatment. The solution after the hydrothermal treatment was a white suspension. The resultant suspension had a pH of 1.4, an electric conductivity of 27.6 mS/cm, a $TiO_2$ concentration of 4.0% by mass, 4.5% by mass of oxalic acid, and a particle diameter based on dynamic light scattering method of 664 nm. Transmission electron microscope observation of the suspension showed an aggregate of spindle-shaped particles of about 100 nm and fine particles of about 5 nm. X-ray diffraction analysis on powder obtained by drying the resultant sol at 110° C. revealed that the powder was a mixture of a rutile type crystal and an anatase type crystal.

Comparative Example 3

65.5 g of pure water was put into a 200 ml beaker, in which mixed with stirring were 0.22 g of metastannic acid (contained in an amount of 0.19 g in terms of $SnO_2$), 22.8 g of 25% by mass tetramethylammonium hydroxide aqueous solution, 7.9 g of oxalic acid dihydrate (contained in an amount of 5.6 g in terms of oxalic acid), and 3.6 g of titanium tetraisopropoxide (contained in an amount of 1.0 g in terms of $TiO_2$). The resultant titanium-containing aqueous solution had a tin atom/titanium atom molar ratio of 0.1, a tetramethylammonium hydroxide/titanium atom molar ratio of 5.0, and an oxalic acid/titanium atom molar ratio of 5.0. 100 g of the titanium-containing aqueous solution was heated at 80° C. for 2 hours. The heated titanium-containing aqueous solution had a pH of 2.9, an electric conductivity of 21.5 mS/cm, and a $TiO_2$ concentration of 1.0% by mass. 60 g of the heated titanium-containing aqueous solution was charged into a 100 ml Teflon (registered trademark) autoclave, was subjected to a hydrothermal treatment at 140° C. for 5 hours, and was then cooled to room temperature after the hydrothermal treatment. The solution after the hydrothermal treatment was a colorless, transparent solution. The resultant solution had a pH of 3.1, an electric conductivity of 22.1 mS/cm, a $TiO_2$ concentration of 1.0% by mass, 5.7% by mass of tetramethylammonium hydroxide, and 5.6% by mass of oxalic acid. Transmission electron microscope observation of the resultant solution showed no titanium oxide particle.

Comparative Example 4

5.8 g of pure water was put into a 200 ml beaker, in which mixed with stirring were 0.89 g of metastannic acid (contained in an amount of 0.75 g in terms of $SnO_2$), 72.8 g of 25% by mass tetramethylammonium hydroxide aqueous solution, 6.3 g of oxalic acid dihydrate (contained in an amount of 4.5 g in terms of oxalic acid), and 14.2 g of titanium tetraisopropoxide (contained in an amount of 4.0 g in terms of $TiO_2$). The resultant titanium-containing aqueous solution had a tin atom/titanium atom molar ratio of 0.1, a tetramethylammonium hydroxide/titanium atom molar ratio of 5.0, and oxalic acid/titanium atom molar ratio of 1.0. 100 g of the titanium-containing aqueous solution was heated at 80° C. for 2 hours. The heated titanium-containing aqueous solution had a pH of 14.0, an electric conductivity of 39.2 mS/cm, and a $TiO_2$ concentration of 4.0% by mass. 60 g of the heated titanium-containing aqueous solution was charged into a 100 ml Teflon (registered trademark) autoclave, was subjected to a hydrothermal treatment at 140° C. for 5 hours, and was then cooled to room temperature after the hydrothermal treatment. The solution after the hydrothermal treatment was a salting-out solution. The resultant solution had a pH of 13.9, an electric conductivity of 42.4 mS/cm, a $TiO_2$ concentration of 4.0% by mass, 18.2% by mass of tetramethylammonium hydroxide, and 4.5% by mass of oxalic acid. Transmission electron microscope observation of the resultant solution showed no titanium oxide particle.

Comparative Example 5

62.8 g of pure water was put into a 200 ml beaker, in which mixed with stirring were 0.089 g of metastannic acid (contained in an amount of 0.075 g in terms of $SnO_2$), 18.2 g of 25% by mass tetramethylammonium hydroxide aqueous solution, 4.7 g of oxalic acid dihydrate (contained in an amount of 3.4 g in terms of oxalic acid), and 14.2 g of titanium tetraisopropoxide (contained in an amount of 4.0 g in terms of $TiO_2$). The resultant titanium-containing aqueous solution had a tin atom/titanium atom molar ratio of 0.01, a tetramethylammonium hydroxide/titanium atom molar ratio of 1.0, and an oxalic acid/titanium atom molar ratio of 0.75. 100 g of the titanium-containing aqueous solution was heated at 80° C. for 2 hours. The heated titanium-containing aqueous solution had a pH of 5.5, an electric conductivity of 21.4 mS/cm, and a $TiO_2$ concentration of 4.0% by mass. 60 g of the heated titanium-containing aqueous solution was charged into a 100 ml Teflon (registered trademark) autoclave, was subjected to a hydrothermal treatment at 140° C. for 5 hours, and was then cooled to room temperature after the hydrothermal treatment. The solution after the hydrothermal treatment was a pale milk white titanium oxide hydrosol. The resultant sol had a pH of 3.9, an electric conductivity of 27.1 mS/cm, a $TiO_2$ concentration of 4.0% by mass, 4.6% by mass of tetramethylammonium hydroxide, 3.4% by mass of oxalic acid, and a particle diameter based on dynamic light scattering method of 21 nm. Transmission electron microscope observation of the sol showed ellipsoidal particles with a minor axis of 10 nm and a major axis of 25 nm and spherical particles of about 5 nm. X-ray diffraction analysis on powder obtained by drying the resultant sol at 110° C. revealed that the powder was a mixture of a rutile type crystal and an anatase type crystal.

Comparative Example 6

94.8 g of pure water was put into a 200 ml beaker, in which mixed with stirring were 0.22 g of metastannic acid (contained in an amount of 0.19 g in terms of $SnO_2$), 1.1 g of 25% by mass tetramethylammonium hydroxide aqueous solution, 0.30 g of oxalic acid dihydrate (contained in an amount of 0.21 g in terms of oxalic acid), and 3.6 g of titanium tetraisopropoxide (contained in an amount of 1.0 g in terms of $TiO_2$). The resultant titanium-containing aqueous solution had a tin atom/titanium atom molar ratio of 0.1, a tetramethylammonium hydroxide/titanium atom molar ratio of 0.25, and an oxalic acid/titanium atom molar ratio of 0.19. 100 g of the titanium-containing aqueous solution was heated at 80° C. for 2 hours. The heated titanium-containing aqueous solution had a pH of 5.0, an electric conductivity of 7.8 mS/cm, and a $TiO_2$ concentration of 1.0% by mass. 60 g of the heated titanium-containing aqueous solution was charged into a 100 ml Teflon (registered trademark) autoclave, was subjected to a hydrothermal treatment at 180° C. for 5 hours, and was then cooled to room temperature after the hydrothermal treatment. The solution after the hydrothermal treatment was a white suspension. The resultant suspension had a pH of 3.9, an electric conductivity of 8.1 mS/cm, a $TiO_2$ concentration of 1.0% by mass, 0.28% by mass of tetramethylammonium hydroxide, 0.21% by mass of oxalic acid, and a particle diameter based on dynamic light scattering method of 702 nm. Transmission electron microscope observation of the sol showed an aggregate of 0.1 μm to 2 μm containing ellipsoidal particles with a minor axis of 10 nm and a major axis of about 25 nm. When the resultant suspension was left at rest, sedimentation and two-layer separation occurred, and the suspension was not a uniform sol. X-ray diffraction analysis on powder obtained by drying the resultant suspension at 110° C. revealed that the interplanar spacing d of the <110> planes was 3.24 Å and that the powder was a single phase of a rutile type crystal.

TABLE 1

| | | Example 1 | Example 2 | Example 3 | Example 4 | Example 5 | Example 6 | Example 7 | Example 8 |
|---|---|---|---|---|---|---|---|---|---|
| Reaction conditions | Sn/Ti molar ratio | 0.1 | 0.1 | 0.1 | 0.1 | 0.1 | 0.05 | 0.7 | 0.1 |
| | $NR_4(OH)^*$/Ti molar ratio | 0.25 | 1.0 | 3.0 | 1.0 | 3.0 | 1.0 | 1.0 | 0.25 |
| | Oxalic acid/Ti molar ratio | 0.19 | 7.0 | 1.0 | 0.75 | 7.0 | 0.75 | 0.75 | 0.19 |
| | Concentration in terms of $TiO_2$ (% by mass) | 4.0 | 1.0 | 2.0 | 4.0 | 1.0 | 4.0 | 4.0 | 1.0 |
| | pH of titanium-containing aqueous solution | 4.2 | 1.4 | 13.5 | 5.5 | 1.3 | 5.5 | 5.5 | 5.0 |
| | Hydrothermal treatment temperature (° C.) | 140 | 140 | 140 | 140 | 140 | 140 | 140 | 100 |
| Sol properties | Particle diameter based on dynamic light scattering method (nm) | 17 | 43 | 28 | 14 | 19 | 15 | 22 | 27 |
| | Crystalline phase | Rutile | Rutile | Rutile | Rutile | Rutile | Rutile | Rutile | Rutile |

| | | Comparative Example 1 | Comparative Example 2 | Comparative Example 3 | Comparative Example 4 | Comparative Example 5 | Comparative Example 6 |
|---|---|---|---|---|---|---|---|
| Reaction conditions | Sn/Ti molar ratio | 0.1 | 0.1 | 0.1 | 0.1 | 0.01 | 0.1 |
| | $NR_4(OH)^*$/Ti molar ratio | 1.0 | 0.0 | 5.0 | 5.0 | 1.0 | 0.25 |
| | Oxalic acid/Ti molar ratio | 0.0 | 1.0 | 5.0 | 1.0 | 0.75 | 0.19 |
| | Concentration in terms of $TiO_2$ (% by mass) | 4.0 | 4.0 | 1.0 | 4.0 | 4.0 | 1.0 |
| | pH of titanium-containing aqueous solution | 13.5 | 1.1 | 2.9 | 14.0 | 5.5 | 5.0 |
| | Hydrothermal treatment temperature (° C.) | 140 | 140 | 140 | 140 | 140 | 180 |
| Sol properties | Particle diameter based on dynamic light scattering method (nm) | 115 | 664 | — | — | 21 | 702 |
| | Crystalline phase | Anatase + rutile | Anatase + rutile | — | — | Anatase + rutile | Rutile |

$NR_4(OH)^*$: Quaternary ammonium hydroxide

INDUSTRIAL APPLICABILITY

The rutile type titanium oxide sol obtained by the present invention is useful for use in catalysts, photocatalysts, optical materials, antibacterial application, antifouling application, and the like and is particularly useful for use in titanium oxide for transparent electrodes for dye-sensitized solar cells.

The invention claimed is:

1. A method for producing a rutile titanium oxide sol having a particle diameter based on dynamic light scattering method of 5 nm to 100 nm, comprising:
   process (a): mixing metastannic acid, a titanium alkoxide, a quaternary ammonium hydroxide, oxalic acid, and water so as to contain 0.02 moles to 0.8 moles of tin atoms, 0.1 moles to 3.5 moles of the quaternary ammonium hydroxide, and 0.1 moles to 8.0 moles of the oxalic acid with respect to 1 mole of titanium atoms of the titanium alkoxide to prepare a titanium-containing aqueous solution with a concentration in terms of $TiO_2$ of 0.1% by mass to 15% by mass; and
   process (b): subjecting the titanium-containing aqueous solution obtained in process (a) to a hydrothermal treatment at a temperature from 100° C. to 170° C.

2. The method for producing a rutile type-titanium oxide sol according to claim 1, wherein
   the titanium alkoxide is a titanium tetraalkoxide of General Formula (I):

$$Ti(OR^1)_4 \qquad (I)$$

where $R^1$ are each a $C_{1-3}$ alkyl group and are the same or different.

3. The method for producing a rutile titanium oxide sol according to claim 1, wherein
the quaternary ammonium hydroxide is a quaternary ammonium hydroxide of General Formula (II):

$$[NR^2R^3R^4R^5]OH \quad (II)$$

where $R^2$, $R^3$, $R^4$, and $R^5$ are each independently a $C_{1-8}$ alkyl group, a $C_{1-8}$ hydroxyalkyl group, a $C_{7-15}$ aryloxyalkyl group, or a benzyl group.

4. The method for producing a rutile titanium oxide sol according to claim 1, wherein
the quaternary ammonium hydroxide is tetramethylammonium hydroxide or tetraethylammonium hydroxide.

* * * * *